Figure 1:
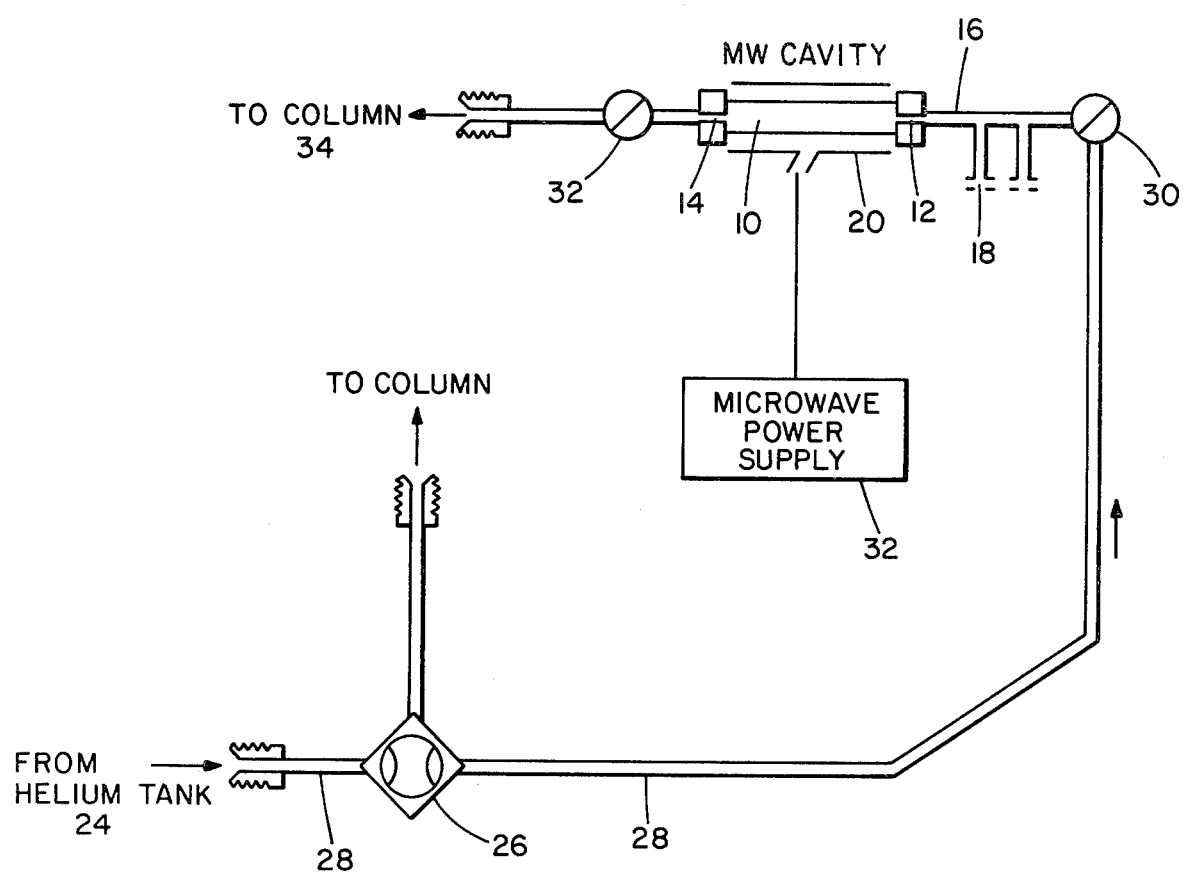

United States Patent [19]
Taylor et al.

[11] 4,330,295
[45] May 18, 1982

[54] MICROWAVE DISCHARGE DEGRADATION OF ORGANICS FOR ANALYSIS

[75] Inventors: James W. Taylor, Madison, Wis.; Romer A. Romero, Maracaibo, Zulia, Venezuela

[73] Assignee: Wisconsin Alumni Research Foundation, Madison, Wis.

[21] Appl. No.: 17,420

[22] Filed: Mar. 5, 1979

[51] Int. Cl.³ ............... G01N 22/00; G01N 30/00
[52] U.S. Cl. ............... 23/230 M; 23/230 PC; 422/80
[58] Field of Search ............... 23/230 PC, 230 M; 422/78, 80, 98

[56] References Cited

U.S. PATENT DOCUMENTS

| | | | |
|---|---|---|---|
| 3,168,378 | 2/1965 | Maresh et al. | 23/230 PC |
| 3,904,366 | 9/1975 | Grasenick | 23/230 PC |
| 4,017,404 | 4/1977 | Habeger | 23/230 PC X |
| 4,148,612 | 4/1979 | Taylor et al. | 422/98 X |
| 4,159,894 | 7/1979 | Hu | 23/230 PC |

OTHER PUBLICATIONS

Fu, "Gasification of Fossil Fuels in a Microwave Discharge in Argon", Chem. Abstract No. 99773n vol. 75, 1971.

Fu, et al., "Gasification of Solid Fuels in a Microwave Discharge", Chemical, Abstract No. 89852y, volume 75, 1971.

Durmosch et al., "Rapid Pyrolysis of Coal by Direct Heating in a Microwave Field", Chem. Abstr. No. 101047u, vol. 82, 1975.

*Primary Examiner*—Arnold Turk
*Attorney, Agent, or Firm*—McDougall, Hersh & Scott

[57] ABSTRACT

The application of continuous microwave discharges in helium to degrade and identify polymer samples coated on a quartz tube positioned in the central portion of the discharge.

4 Claims, 6 Drawing Figures

MICROWAVE DISCHARGE DEGRADATION OF ORGANICS FOR ANALYSIS

This invention relates to a method of analysis of organic materials, and it relates more particularly to a method and means for converting high molecular weight polymers and samples into volatile products or components of which the polymer or sample is formed for subsequent analysis by conventional techniques, such as gas chromatography and mass spectrometry.

One technique that has been widely adopted for analysis of relatively non-volatile samples is known as "pyrolysis gas chromatography" (PGC) which operates, primarily by "fingerprint" comparison of the chromatographic peaks of the degradation products of the non-volatile material to be diagnosed.

One of the most suitable uses of pyrolysis gas chromatography is for the analysis and characterization of polymers. The earliest studies for polymers involved single flow systems in which the identity of the small and large components of the pyrolyzate could not be determined simultaneously. The technique has been improved and can now be used in even microstructural studies of hydrocarbon polymers, along with the sequence distribution dyads in several vinyl-type copolymers, including styrene-chlorostyrene copolymers, acrylonitrile-chlorostryrene copolymers, and acrylonitrile-styrene and acrylonitrile-methyl acrylate copolymers.

The history of pyrolysis gas chromatography has been characterized as a continual search for the perfect pyrolysis unit capable of producing reproducible results from one laboratory to another. Several approaches have been taken to overcome the difficulties, such as the use of the Curie-point pyrolyzer, sealed sample holders and multicolumn systems, but the overall problem has not been solved. For instance, the Curie-point pyrolyzer, which is considered to have significant advantages over the more common filament pyrolysis systems, is based on the equilibrium pyrolysis temperature. However, the critical parameter in pyrolysis is the rate of heat transfer to the sample and not the equilibrium pyrolysis temperature. Thus, variations in sample size, timing in applying the heat, entrapped solvent, and the thermal conductivity of the sample are sources which lead to non-reproducible data.

Use has been made of laser heat to pyrolyze samples. The newer method is called Laser Pyrolysis Gas Chromatography (LPGC) wherein gas chromatography is retained as the best way to achieve the separation of the final degradation products.

Although laser pyrolysis appears advantageous, one problem is associated with the way the energy is absorbed. In some cases, the use of additives (i.e., carbon or metal powder) is needed to maximize absorptivity. With the neodymium-glass system, slight changes in beam focus produce substantially different pyrolysis patterns, and the fragmentation pattern is strongly dependent upon the laser beam energy. When additives for increased absorptivity are employed, these are also dependent on the concentration of added carbon or metal. There is also dependence on sample color.

Photolytic degradation has been proposed as a more reproducible substitute for all techniques dependent upon thermal degradation. Photochemical degradation was shown to be an acceptable approach for the determination of triglyceride ester, and of ethyl fluoride at 147 nm. However, considerable disagreement is raised concerning mechanisms, quantum efficiency, and even the products formed from a given polymer when photolysis gas chromatography is employed; variations in surface state of the sample, impurities, and crystallinity affect the results to a large extent.

It is an object of this invention to provide a pyrolysis/degradation technique which is more versatile than the filament heater, the ruby laser, or the photolytic technique.

More specifically, it is an object of this invention to provide a gas microwave discharge as heat, light, and electron sources which, through degradation, can be used to characterize polymers and other organic materials.

Figure 2:
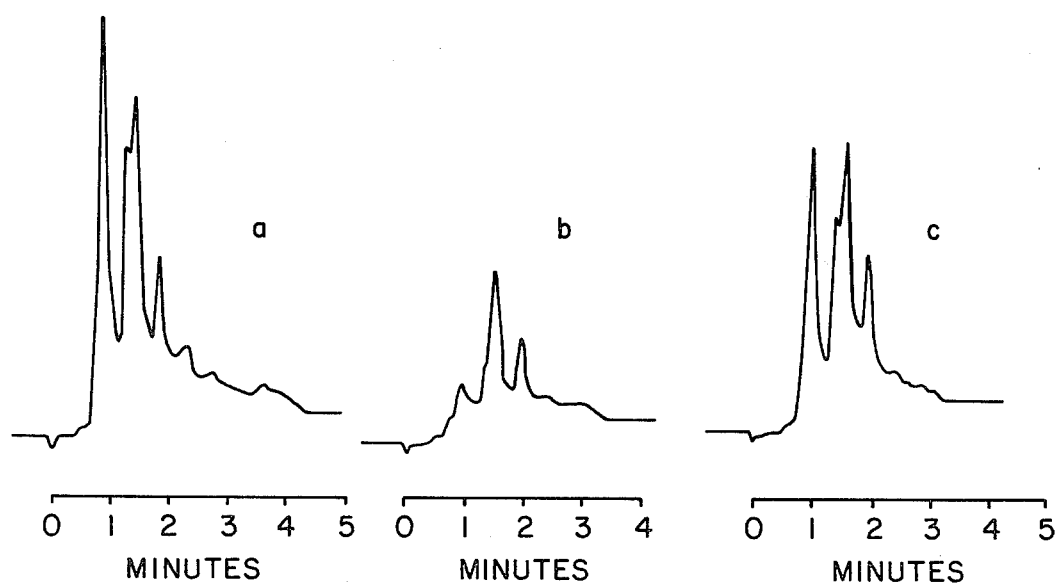
Figure 3:
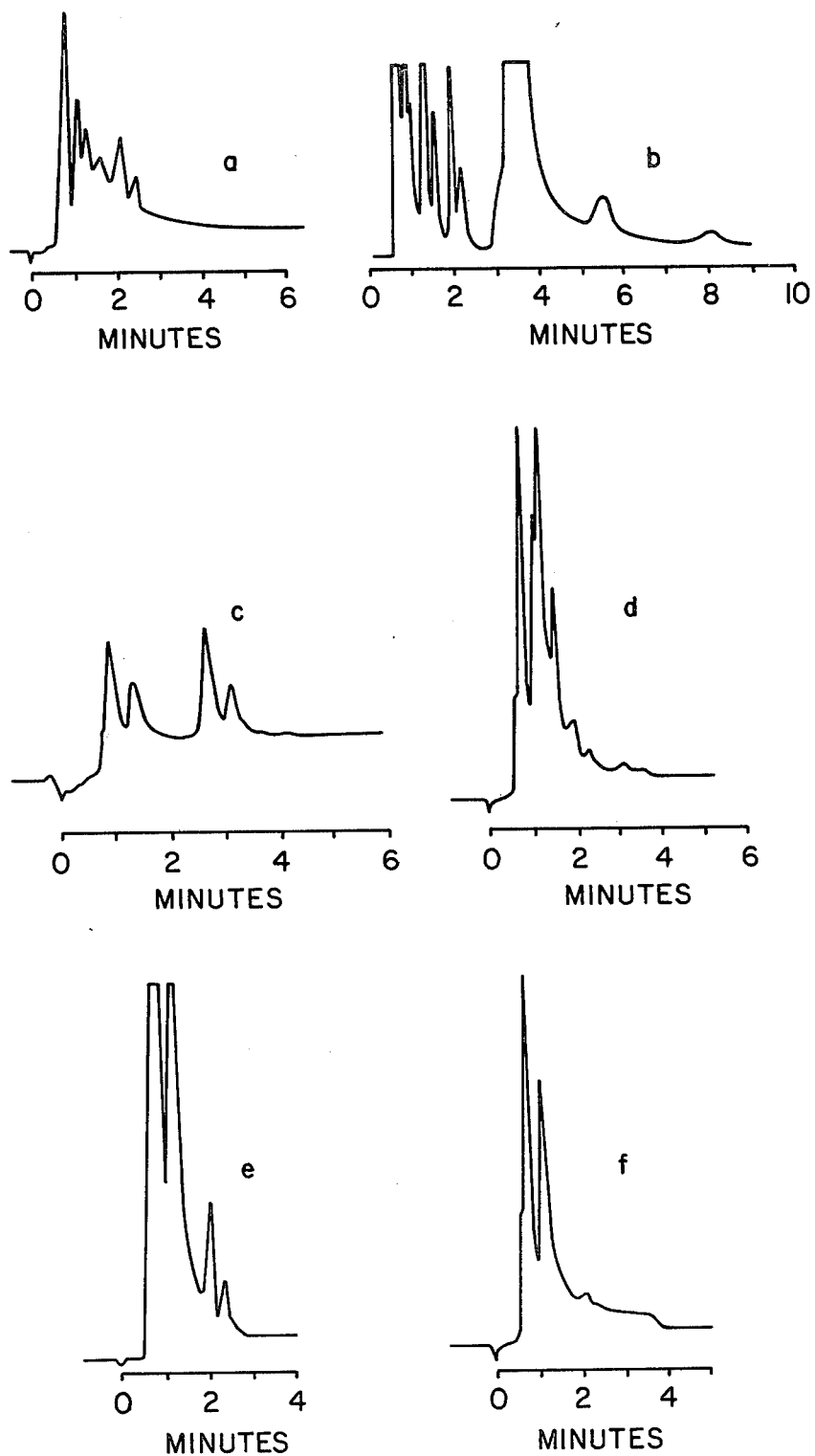

These and other objects and advantages of this invention will hereinafter appear and, for purposes of illustration, but not of limitation, reference will be made to the accompanying drawings in which:

FIG. 1 is a schematic outline of a microwave discharge system employed in the practice of this invention;

FIG. 2 are continuous microwave degradation chromatograms of polycarbonate at (a) 1 torr pressure and 5 second continuous wave discharge times; (b) 1 torr and 2 seconds, and (c) 100 torr and 10 seconds;

FIG. 3 show continuous microwave degradation chromatograms for polymers obtained at 100 torr and 15 seconds (a) polystyrene MW 2,100; polystyrene MW 321,00; (c) polystyrene MW 670,000; (d) polycarbonate resin MW 33,800; (e) polyvinyl chloride MW 83,500; (f) polyvinyl fluoride MW 126,000.

Figure 4:
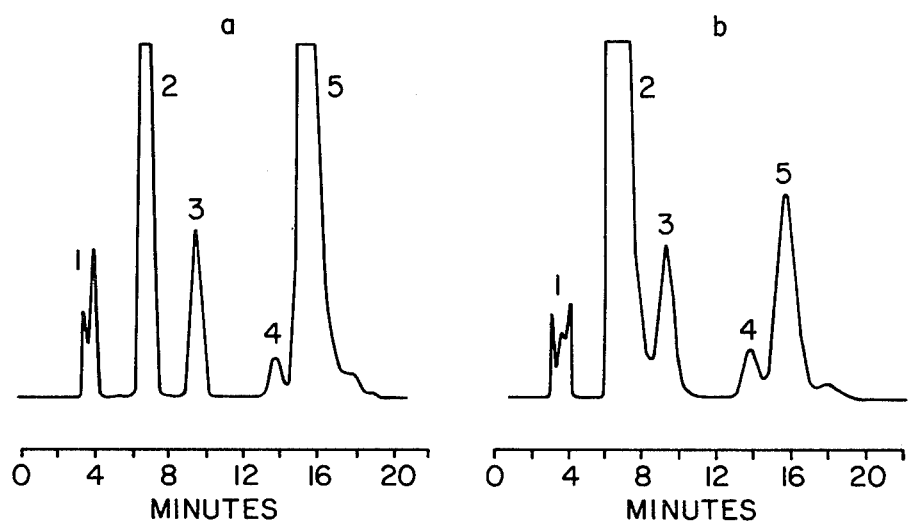
Figure 5:
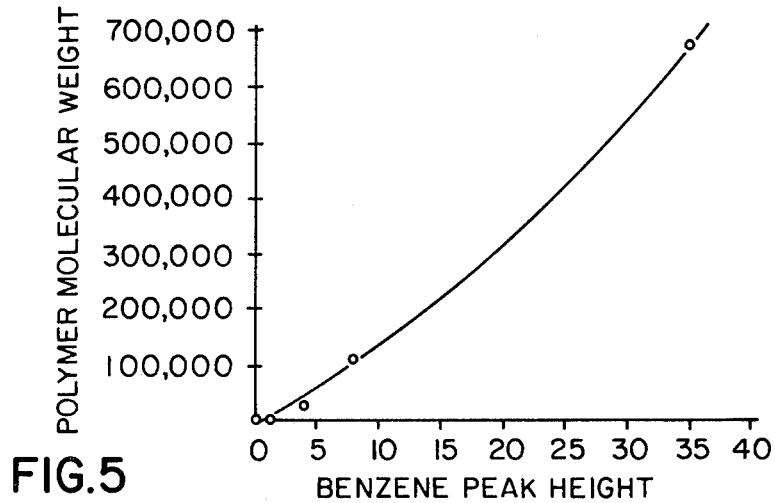
Figure 6:
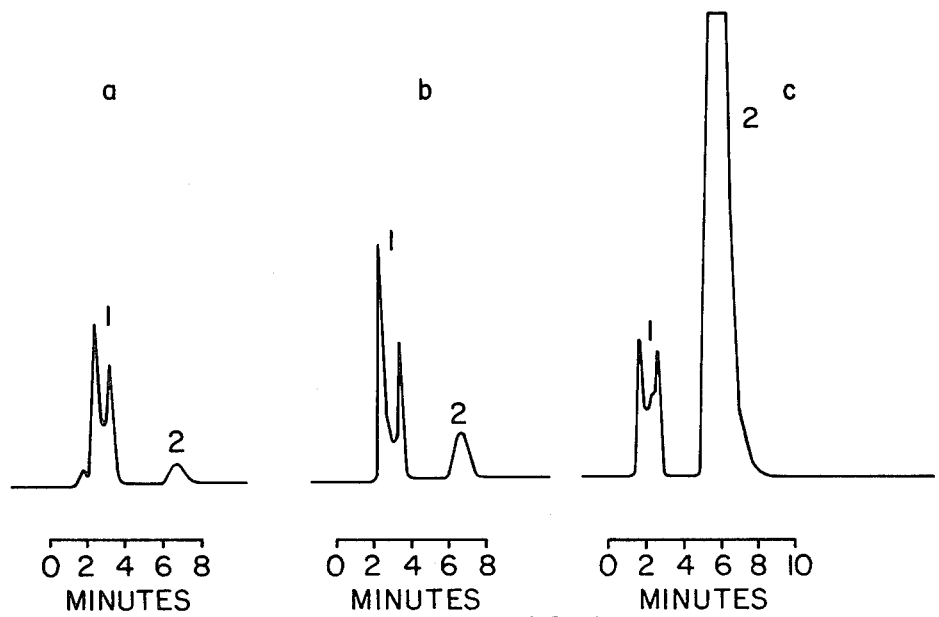

FIG. 4 shows total ion current chromatograms of polystyrene (MW 37,500) degraded by continuous microwave radiation; (a) at 100 torr and 25–30 seconds; (b) 1.0 torr and 10 seconds. Peak identification 1=mixture of volatile compounds (methane, ethylene); 2=benzene; 3=toluene; 4=ethyl benzene; 5=styrene;

FIG. 5 shows effect of variations in polymer molecular weight on height of benzene peak for polystyrene (MW 321,000) degraded by continuous microwave radiation at 15 seconds at 100 torr helium pressure; and FIG. 6 shows total ion current chromatograms of polyvinyl chloride degraded by 100 torr continuous microwave discharge under different exposure times of (a) 5 seconds; (b) 10 seconds; (c) 15 seconds with peak identification of 1=mixture of $CH_4$, HCl, $CO_2$, $H_2O$, etc.); 2=ethylene chloride.

The technique of this invention is schematically illustrated in FIG. 1 of the drawings, in which a discharge tube 10, such as a pyrex tube, is provided with an inlet 12 at one end and an outlet 14 at the other, with the inlet connected by a passage 16 to an evacuating pump 18, such as a two-stage mechanical pump. Discharge pressure within the tube 10 is measured by a suitable pressure gauge, such as a General Electric thermistor vacuum gauge with a calibrated gauge. The discharge tube 10 is surrounded by a microwave cavity 20 connected to a microwave power supply 22. The pump operates to pump air out of the discharge tube 10 before helium gas or other inert gas is admitted from a helium source 24.

Once the microwave discharge is ignited in the helium, the discharge can be maintained for various periods of time, then the helium is flowed through the discharge tube by switching the helium flow orientation with the two-way valve 26 in the line 28 connecting the helium source 24 with the discharge tube 10. Helium becomes the carrier gas during the subsequent chromatographic separations.

Before igniting the microwave discharge, valves 30 and 32 in the passages communicating with the inlet 12 and outlet 14, respectively, were closed. After the discharge was terminated, valve 26 was oriented to direct the helium flow through the discharge tube, valves 30 and 32 were opened, and the microwave degradation products were swept into the chromatographic column 34. After a short time, such as 30 to 40 sec, valve 32 is closed and the two-way valve is again oriented to direct the helium flow to the normal route in the gas chromatograph.

The polymer sample to be analyzed is preferably coated from a solvent solution, as by dipping, to provide a thin film on a tube, such as a quartz capillary tube (similar to those used for fusion) or it may be analyzed in a solid form such as a thin filament or a small bead. The sample is supported as close to the center of the discharge tube as possible as by using a nichrome spring, which was never under microwave exposure. The sample is maintained at about the center of the tube because there the microwave discharge intensity is greater than at the walls.

It is preferred to make use of continuous microwave discharge although pulsed discharge has limited use. By way of illustration in an experimental configuration, use was made of a 100 watt, 2.45 GHz diathermy unit (Burdick model MW/200) modified to measure the forward (applied) and reverse (reflected) power (Bendix Micro Match power meter model 7253) generated the continuous microwave irradiations used to degrade the polymers. A McCarroll-type cavity was connected directly to the power supply by a coaxial cable. It is not possible to tune the cavity to reflect zero power with this power supply, but measurements of the reflected power indicated that about 27% of the total applied power was dissipated in the discharge. The forward power oscillated between 55 and 70 watts, and the reflected power oscillated between 12 and 20 watts, when the power control was set at 80% of total power.

For separations by gas chromatography, use can be made of conventional gas chromatography equipment and methods, such as an F&M Model 720 gas chromatograph with an F&M Model 1609 flame ionization attachment or a gas chromatograph/mass spectrometer (GC/MS) system for the separation and identification of the microwave degradation fractions from polymers or other organic products.

In the experimental studies made in the development of this invention, use was made of a Varian aerograph series 1700 (Model 1740) gas chromatograph coupled directly to a Varian Mat CH 7 mass spectrometer. The chromatographic column was a 6-foot stainless steel column packed with 15% SE-30 on Chromosorb P (HMDS). In the whole experimental sets, the separations were run isothermally with oven temperature of 110° C. The injection port and detector temperature were 180° C. and 210° C., respectively. The carrier gas flow was set at 45 cc/min.

The microwave degradation products from experimental sets were also trapped before insertion into the F&M gas chromatograph. For this purpose, the discharge tube was closed at the end that connected to the injection port. A 2 cm long, ½ cm ID tube was sealed onto the discharge tube, 2 cm away from the closed end, and a ¼ inch Cajon union permitted attachment of a vial, which had a capillary stopcock attached to this side tube. Before the microwave discharge ignition, the vial with the stopcock open was cooled with a liquid nitrogen bath for 10 min. After the discharge was extinguished, the open vial was kept in the bath for 5 additional min. After closing the stopcock, the vial was heated at 170° C. for 3 min. A 10 ml Hamilton gas-tight syringe was used to sample the vial through an adapted septum, and to inject in the GC/MS.

The invention has been successfully applied with various representative polymers of varying molecular weights, such as polystyrenes in molecular weight of 2,100; 10,000; 37,000; 321,000; and 670,000; polycarbonate resin 38,000 molecular weight, polyvinyl chloride having a molecular weight of 83,500 and polyvinyl fluoride having a molecular weight of 126,000. It will be understood that the invention is equally applicable for the analysis of other polymers and organic compounds. All the molecular weights, except the one for fluoride, were determined by light scattering. Polyvinyl fluoride molecular weight was calculated by gel permeation chromotography (GPC). Benzene was the selected solvent for the polystyrenes although methyl ethyl ketone was also employed. For polyvinyl fluoride, benzene was also used, but the samples did not dissolve completely. Tetrahydrofuran was the solvent for polyvinyl chloride, and methylene chloride was used to prepare the polycarbonate resin solutions.

Both the discharge and the observed products of the microwave radiation are influenced by a number of parameters, such as (1) pressure in the discharge tube, (2) discharge exposure time, (3) sample position in the discharge tube, and (4) discharge tube size, especially the inside diameter. For continuous microwave radiation there is a direct proportionality between pressure at which the microwave ignites and the intensity of the microwave radiation, which was followed down to 0.01 torr. Above 500 torr and below 0.5 torr of helium pressure, the discharge extinguished. At fixed pressure, the longer the discharge exposure on the sample the more extensive the degradation. At any pressure in between (500 to 0.5 torr) and from 0.5 sec to 30 sec, reproducible degradation patterns (i.e., chromatographic peaks) can be obtained when using continuous microwaves.

An appropriate combination of discharge pressure and time is desirable so that the polymer could be degraded in such a fashion that its identification and characterization would be accomplished along with the formulation of possible degradation pathways. With gas chromatography alone, it was found that degradation of polystyrene leads to two major peaks (which might contain one or more components), with retention times of about 45 and 75 sec, respectively. Similar behavior was noted with polycarbonate resin, but the products appeared at 75 and 90 sec, respectively. FIG. 2 shows the differences in patterns of polycarbonate resin which appear by changing pressure and time. In FIGS. 2a and 2b the helium pressure was maintained constant at 1 torr; the chromatogram on FIG. 2a was produced when the continuous microwave was kept on the sample for 5 sec; in FIG. 2b the exposure time was 2 sec. In FIG. 2c the helium pressure was 100 torr and the exposure time was 10 sec. It will be seen from the data that more complete degradation occurred as the time of discharge increased, but also there was a relationship between time and pressure of the discharge. To achieve the same relative degree of degradation, it was possible to compensate for a long exposure time (e.g., 10 sec) by using a high discharge pressure (e.g., 100 torr).

As can be seen from FIG. 2, intense continuous microwave degradation, which occurred at long periods of exposure time and/or low pressures, led to early peaks. In contrast, mild continuous microwave degradation, e.g., short times and/or high pressures, led to late peaks with retention times over 2 min, when using the F&M gas chromatograph separation system.

FIG. 3 shows the continuous microwave degradation chromatograms obtained for some polymers: polystyrene MW 2,100 (FIG. 3a), polystyrene MW 321,000 (FIG. 3b), polystyrene MW 670,000 (FIG. 3c), polycarbonate resin (FIG. 3d), polyvinyl chloride (FIG. 3e), and polyvinyl fluoride (FIG. 3f). These are characteristic to enable use for their identification. All the chromatograms were produced from discharges with 100 torr of helium and 15 sec of exposure time. 100 torr and about 15 sec were found to be reasonable values in order to achieve reproducible degradation patterns for the limited number of polymers sought to be characterized.

Radiation has different effects on the sample depending on the sample position in the discharge tube. On this point, it was found that the microwave discharge does not cause as extensive a sample degradation at the discharge tube walls as it does to a sample held at the center.

Products resulting from the microwave degradation of polystyrene (MW=321,000) were trapped by using the trapping system previously described. Then they were separated and identified by GC/MS. Three major peaks were revealed, which where benzene, toluene, and styrene, and minor components associated with the air peaks, such as methane, water, ethylene, acetylene, and carbon dioxide. The microwave discharge system described in FIG. 1 was coupled directly to the Varian Aerograph gas chromatograph which, in turn, was coupled through a Bieman-Watson separator to the CH-7 mass spectrometer.

FIG. 4 shows two chromatograms of the same polymer (polystyrene 321,000) carried out under different conditions of time and pressure. FIG. 4a was obtained under the conditions of 100 torr and 25-30 sec, and FIG. 4b was obtained at 1.0 torr and 10 sec. Both conditions led to the same degradation pattern: a mixture of volatile compounds (peak 1), benzene (peak 2), toluene (peak 3), ethyl benzene (peak 4) and styrene (peak 5). It will be apparent that two different pressures may produce the same continuous microwave degradation chromatograms by adjusting the time to an equivalent compensatory value.

The amount of benzene rings in polystyrene should increase when the molecular weights increase. If the benzene peak does arise as the result of a degradation process, it might be expected to increase with the molecular weight of the polymer. FIG. 5 is a plot of polymer molecular weight against benzene peak heights, which is linear over a large region, suggesting that free H or H. might have participated in the benzene production. The highest point in the curve, corresponding to the molecular weight 670,000, was obtained with a polymer sample dissolved in methyl ethyl ketone to ensure that benzene, as a solvent, was not trapped in the polymer even after drying the sample on the capillary tube. Styrene also showed a relationship to molecular weight, but no relationship was found when plotting polymer molecular weights against toluene peak heights.

From continuous microwave degradation experiments of polystyrene, a consistent pattern related to the structure of the sample was noted. If polyvinyl chloride and polycarbonate resin followed the same degradation patterns, one would expect to find monomer peaks in their total ion current chromatograms and their correspondent mass spectra. FIG. 6 shows the results obtained from polyvinyl chloride. The only major peak was ethyl chloride and, depending on the exposure time of the microwave discharge, its size was variable. A short time led to a smaller peak than that obtained by using a longer exposure time. According to this observation, continuous microwave discharge was able to cleave the polymer in monomer fragments, which were volatile enough to be swept by helium into the chromatographic column. Similar patterns were followed by polycarbonate resin. These examples confirm that continuous microwave degradation can be used to identify polymers, since in most cases they lead to the basic monomer components. For instance, in the case of polystyrenes, styrene is obtained as one of the degradation products. For polyvinyl chloride, ethyl chloride was obtained, and for polycarbonate resin, the monomer also appeared.

The sample loading on the capillary appears to be an experimental variable. Excessive sample does not allow the ignition of the discharge, or if it occurs, it is difficult to maintain the discharge. To determine the optimum loading, experiments were conducted in which the only variable was the amount of polymer coated on the capillary. From about 6 mgs to 30 mgs, the discharge ignited rapidly, was stable, and the detection at the mass spectrometer was reasonably high in relation to the amount of analyzed sample. From these results, determinations were made of the percentage of the sample actually degraded. By weighing the capillary tube with and without the polymer on it, the difference between these two values as the absolute weight of polymer undergoing the continuous microwave degradation could be determined. After extinguishing the discharge, the capillary tube was weighed again and the sample that remained. From this value, it was determined that about 55-60% of sample was degraded when continuous microwave radiation was maintained for 15 sec. From this observation, it was estimated that some of the degradation and cleavages occurred in the gas phase after the production of the first compounds occurred. The above percentage does not indicate the total amount of products going onto the GC/MS because it will also be influenced by condensation on the tube walls.

From the foregoing, it will be apparent that continuous microwave radiation can be extended to other fields of the analysis of high molecular weight compounds. This approach has much to offer with respect to other techniques because the patterns produced are much simpler, and the sample loading is easy and direct.

While helium is the more energetic carrier gas for use in the practice of this invention, other inert excitable gases can be used such as neon and argon, with the former being preferred as more energetic than the latter.

It is desirable to arrange the small tube containing the sample to be analyzed, preferably centered within another tube of larger diameter, such as the cavity, through which the helium is circulated so that the sample will not be subjected to thermal degradation, as when the sample is not protected by such concentric tube.

We claim:

1. A method of analysis of organic materials comprising the steps of depositing the organic material to be analyzed as a thin coating on a support located in a central portion of a discharge tube, supporting the said tube in a microwave cavity, exhausting air from the discharge tube, filling the discharge tube with helium gas, subjecting the organic material to a combination of microwave excitation and photon degradation by exposing the material to microwave discharge in helium gas at a pressure within the range of 0.5–500 Torr. and for a time within the range of 0.5–30 seconds, and sweeping the tube with an inert gas for removal of degradation products for separate determination.

2. The method as claimed in claim 1, in which the discharge tube is a glass pyrex tube.

3. The method as claimed in claim 1, in which the organic material is an organic polymer and the organic polymer is provided as a solution which is then evaporated leaving a thin film coating on the support.

4. The method as claimed in claim 1, in which the degradation products from microwave degradation are collected for separation by gas chromatography.

* * * * *